(12) United States Patent
Heppe et al.

(10) Patent No.: US 9,731,086 B2
(45) Date of Patent: Aug. 15, 2017

(54) DEVICE FOR DETECTING MOISTURE FOR AN ARRANGEMENT FOR MONITORING AN ACCESS TO A PATIENT

(71) Applicant: Fresenius Medical Care Deutschland GmbH, Bad Homburg v.d.H. (DE)

(72) Inventors: John Heppe, St. Wendel (DE); Andrea Kraemer, Frankfurt am Main (DE); Alexander Schroers, Frankfurt (DE); Andreas Wuepper, Buettelborn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/930,152

(22) Filed: Jun. 28, 2013

(65) Prior Publication Data

US 2014/0012197 A1    Jan. 9, 2014

Related U.S. Application Data

(60) Provisional application No. 61/669,186, filed on Jul. 9, 2012.

(30) Foreign Application Priority Data

Jul. 9, 2012    (DE) .................... 10 2012 013 474

(51) Int. Cl.
*A61M 5/50*    (2006.01)
*A61M 1/36*    (2006.01)
(Continued)

(52) U.S. Cl.
CPC .......... *A61M 5/5086* (2013.01); *A61F 13/42* (2013.01); *A61F 13/45* (2013.01); *A61M 1/3656* (2014.02);
(Continued)

(58) Field of Classification Search
CPC ............ A61M 5/5086; A61M 5/16831; A61M 5/158; A61M 1/3653; A61M 1/367;
(Continued)

(56) References Cited

U.S. PATENT DOCUMENTS 4,733,383 A * 3/1988 Waterbury ............. G04G 21/02
368/10
6,072,392 A * 6/2000 Henderson ............... G08B 1/08
340/539.15
(Continued)

FOREIGN PATENT DOCUMENTS

DE    43 11 947 A1    6/1994
DE    690 14 264 T2    4/1995
(Continued)

OTHER PUBLICATIONS

International Search Report, dated Sep. 4, 2013, from corresponding International Application No. PCT/EP2013/001842.
(Continued)

*Primary Examiner* — Hezron E Williams
*Assistant Examiner* — Marrit Eyassu
(74) *Attorney, Agent, or Firm* — Kilyk & Bowersox, P.L.L.C.

(57) ABSTRACT

A device for detecting moisture for an arrangement for monitoring an access to a patient for a system by which, via a flexible line, a liquid is fed to a patient and/or a liquid is fed out from the patient, and in particular for monitoring the vascular access in extra-corporeal blood treatment and particularly for monitoring a central venous catheter for acute dialysis includes at least a portion which can be deformed into a sleeve and placed around the circumference of the flexible line or of a connecting system. The portion in sleeve form has fastening means for fixing it in place in the position in which it surrounds the flexible line or the connecting
(Continued)

system. The portion in sleeve form allows the device to be fastened quickly and securely to a flexible line or a connecting system.

13 Claims, 4 Drawing Sheets

(51) Int. Cl.
*G01N 27/04* (2006.01)
*A61F 13/42* (2006.01)
*A61F 13/45* (2006.01)
*G01N 27/12* (2006.01)

(52) U.S. Cl.
CPC ......... *G01N 27/048* (2013.01); *G01N 27/121* (2013.01); *A61F 2013/424* (2013.01); *A61M 2205/15* (2013.01)

(58) Field of Classification Search
CPC ............ A61M 1/30; A61M 2205/15; A61M 2001/3656; A61M 2005/1588; A61M 2205/14
USPC ..... 73/73; 604/6.16, 111, 4.01, 288.01, 246, 604/31, 318, 361, 523, 65; 600/371, 362
See application file for complete search history.

(56) References Cited

U.S. PATENT DOCUMENTS

| 6,143,090 | A | 11/2000 | Lietz | |
|---|---|---|---|---|
| 6,664,439 | B1* | 12/2003 | Arndt et al. | 604/378 |
| 8,529,490 | B2* | 9/2013 | Wariar et al. | 604/6.16 |
| 8,696,571 | B2* | 4/2014 | Marttila et al. | 600/371 |
| 2001/0035443 | A1* | 11/2001 | Jones | A45C 1/04 224/222 |
| 2002/0198483 | A1* | 12/2002 | Wariar et al. | 604/5.01 |
| 2005/0177051 | A1* | 8/2005 | Almen | A61B 5/02405 600/509 |
| 2006/0069339 | A1* | 3/2006 | Moll | 604/6.01 |
| 2008/0103424 | A1* | 5/2008 | Ball | A61F 5/0118 602/22 |
| 2010/0271212 | A1* | 10/2010 | Page | 340/573.1 |
| 2011/0217877 | A1* | 9/2011 | Linz | 439/625 |
| 2012/0165772 | A1* | 6/2012 | Groosman et al. | 604/361 |
| 2013/0012881 | A1* | 1/2013 | Lacy | 604/164.08 |
| 2013/0053754 | A1 | 2/2013 | Heppe | |
| 2014/0296808 | A1* | 10/2014 | Curran et al. | 604/361 |

FOREIGN PATENT DOCUMENTS

| DE | 101 26 693 A1 | 12/2002 |
|---|---|---|
| DE | 20 2006 015 100 U1 | 1/2007 |
| DE | 10 2010 012 545 A1 | 9/2011 |
| EP | 0418209 A1 | 3/1991 |
| EP | 0 880 767 B1 | 1/2000 |
| EP | 1262757 A2 | 12/2002 |
| EP | 1 522 836 A2 | 4/2005 |
| WO | 99/24145 A1 | 5/1999 |
| WO | 2008/021462 A2 | 2/2008 |
| WO | 2009/075592 A2 | 6/2009 |

OTHER PUBLICATIONS

International Preliminary Report on Patentability and Written Opinion dated Jan. 13, 2015 in International Application No. PCT/EP2013/001842.

* cited by examiner

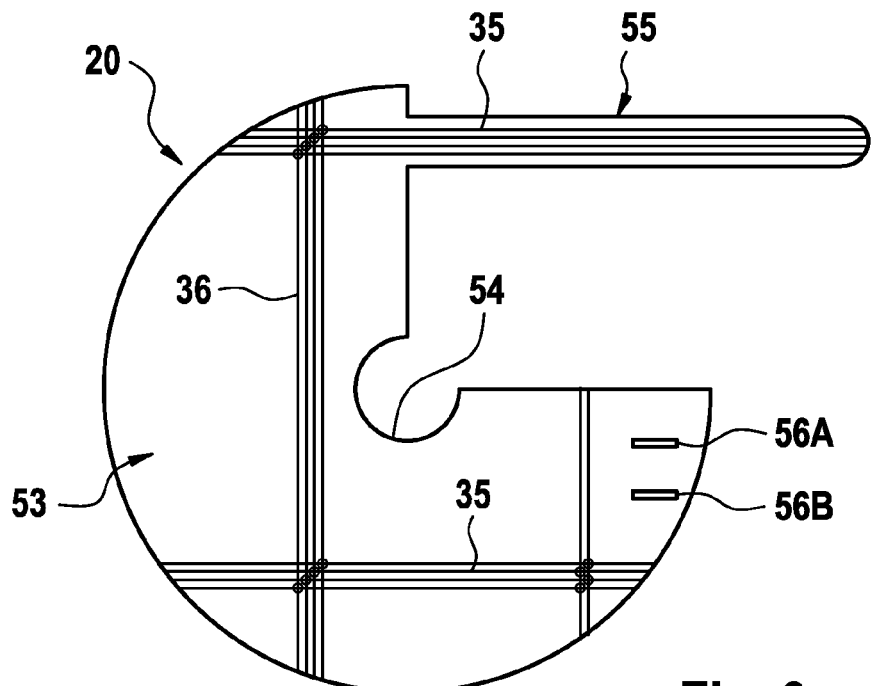
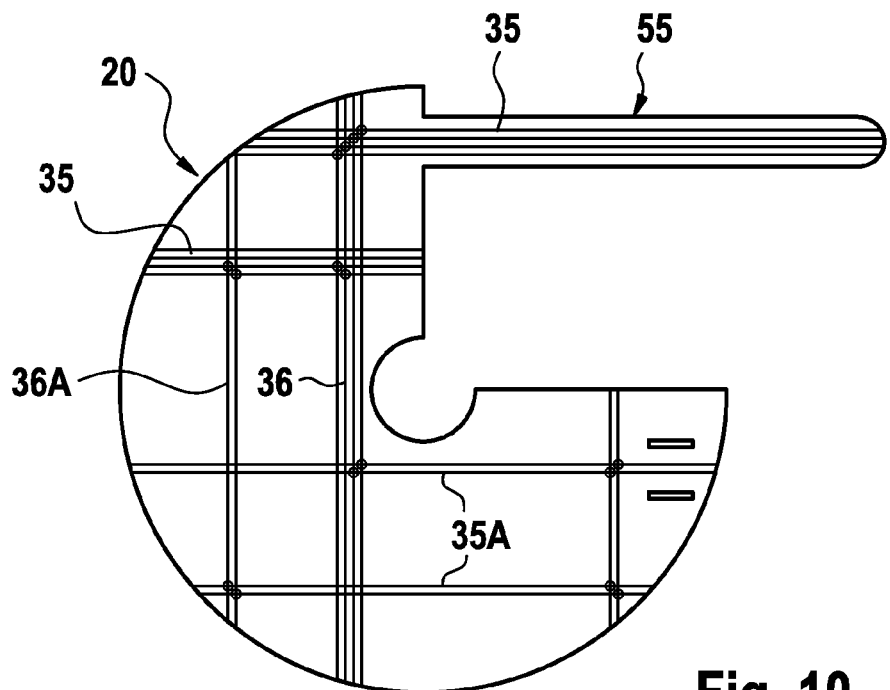

DEVICE FOR DETECTING MOISTURE FOR AN ARRANGEMENT FOR MONITORING AN ACCESS TO A PATIENT

CROSS REFERENCE TO RELATED APPLICATIONS

The present application claims priority to U.S. Provisional Patent Application Ser. No. 61/669,186, filed on Jul. 9, 2012, and Application No. DE 10 2012 013 474.6, filed in the Federal Republic of Germany on Jul. 9, 2012, each of which is expressly incorporated herein in its entirety by reference thereto.

FIELD OF INVENTION

The present invention relates to a device for detecting moisture for an arrangement for monitoring an access to a patient for a system by which, via a flexible line, a liquid is fed to a patient and/or a liquid is fed out from the patient, and in particular for monitoring the vascular access in extra-corporeal blood treatment and particularly for monitoring a central venous catheter in acute dialysis. As well as this, the present invention also relates to an arrangement for monitoring an access to a patient which has a device for detecting moisture.

BACKGROUND INFORMATION

In the field of medical engineering, there are various known systems with which, via a flexible line, liquids can be withdrawn from patients or liquids can be fed to patients. The access to the patients is generally gained in this case by a catheter for insertion in organs of the body or by a needle for puncturing vessels. During the examination or treatment, it has to be ensured that proper access exists to the patient. It is therefore necessary for the patient access to be monitored.

Proper access to the patient is also a particular prerequisite for the pieces of extra-corporeal blood treatment apparatus which have an extra-corporeal blood circuit. The known pieces of extra-corporeal blood apparatus include for example pieces of dialysis apparatus and cell separators which require access to the patient's vascular system. In extra-corporeal blood treatment, blood is withdrawn from the patient along a flexible arterial line having an arterial puncturing needle and is fed back to the patient along a flexible venous line having a venous puncturing needle. In acute dialysis at intensive care stations on the other hand, what is used as a patient access is for example a central venous catheter in the patient's neck.

What is generally used to connect catheters and flexible lines for making a patient access is the Luer connecting system which is well known in the medical field and whose connecting parts comprise an inner and an outer cone which form tapers. This connecting system is referred to as a Luer lock connection when, to secure the connection, the inner and outer cones are supplemented with a screw thread. Although Luer lock connections provide a very high level of safety, it has been found in practice that the connecting parts, if not properly handled or if used too often or if there are faults in their material, may become disconnected or micro-cracks may develop in the material. U.S. Patent Publication No. 2010/0228231 therefore proposes securing the connecting parts of a Luer lock connecting system against unintentional disconnection with an additional means of fixing the connecting parts.

There are various known arrangements of different forms for monitoring the vascular access. These known monitoring arrangements generally rely on the safety devices which are provided as standard in the pieces of blood treatment apparatus and which trigger an immediate shutoff of the extra-corporeal blood circuit if there is not a proper vascular access.

There are known arrangements for monitoring a vascular access by a needle which have a device for detecting moisture to enable the escape of blood to be detected at the site of the puncture. The known devices for detecting moisture which are used in the known monitoring arrangements for the patient access take the form of a pad which consists of an absorbent material in which is embedded a moisture sensor.

Pads of an absorbent material which are applied to the patient's skin are described in, for example, International Patent Publication No. WO 2006/008866, U.S. Patent Publication No. 2005/0038325 and U.S. Pat. No. 6,445,304. The characteristic feature of the known pads is that the moisture sensor is embedded in the absorbent material and the absorbent material is applied to the patient's skin.

International Patent Publication No. WO 99/24145 describes a device for detecting moisture which has a housing, able to be closed off with a lid, in which a moisture sensor is arranged. Provided in the housing are apertures for the needles and flexible lines to pass through. It is a disadvantage that the housing containing the moisture sensor is relatively expensive to produce in large numbers and is relatively difficult to handle in practice.

SUMMARY

An object underlying the present invention is to provide a device for detecting moisture which can be inexpensively produced in large numbers. A further object of the present invention is to provide a device for detecting moisture which is easy and safe to handle and which is very comfortable to be carried on the patient. Underlying the present invention is also the object of providing an arrangement for monitoring an access to a patient which has a device of this kind for detecting moisture.

The device according to the present invention for detecting moisture has a moisture sensor which takes the form of an electrically conductive structure. The moisture sensor of the device according to the present invention is connected to an arrangement for monitoring an access to a patient which may be part of a system by which, via a flexible line, a liquid is fed to a patient and/or a liquid is fed out from the patient.

The device according to the present invention for detecting moisture is characterised in that at least a portion of the device for detecting moisture takes the form of a portion which can be deformed into a sleeve and which can be placed around the circumference of the flexible line and/or of a system for connecting the flexible line. The portion in sleeve form has fastening means for fixing the portion in sleeve form in place in the position in which it surrounds the flexible line or the connecting system.

The portion formed after the fashion of a sleeve allows the device for detecting moisture to be fastened quickly and securely to a flexible line or to a system for connecting the line. No additional fastening means are required for this purpose. It is not for example necessary for the device to be fixed to the flexible line, the connecting system or the patient's skin with adhesive tape. This simplifies the handling of the device.

As well as this, it is also of advantage for the device according to the present invention to be easily able to be removed again from the flexible line after the treatment, which is important particularly when it is used to monitor a central venous catheter. The device can easily be detached from the flexible line even during the treatment.

In particular, the device according to the present invention can be fastened in place in that region of the flexible line in which a connecting system, such as a Luer connecting system for example, is situated. For this purpose, the portion able to be deformed into a sleeve simply needs to be placed around the connecting system, thus enabling the point of connection to be monitored for leaks.

The device according to the present invention preferably has a layer not permeable to liquid which is adjacent the patient and situated on the outside and a layer absorbent of liquid which is remote from the patient and situated on the inside. What is achieved in this way is that blood escaping at the point of the connection in the flexible line finds its way directly to the moisture sensor. It also prevents sweat from the patient's skin, or blood from a wound or from a leak in the set of blood tubing at some point other than the venous access, or some other liquid from outside finding its way to the moisture sensor, thus preventing false alarms.

Whereas an additional means of securing a Luer connection which is described in U.S. Patent Publication No. 2010/0228231 is only able to prevent the connection from disconnecting, the device according to the present invention also enables a slow loss of blood to be detected, due for example to errors in making the connection in the flexible line or to faults in the material.

In a preferred exemplary embodiment, the connecting means of the portion able to be deformed into a sleeve have at least one elongated portion and at least one slot for the elongated portion to be pulled through. The elongated portion simply has to be pulled through the slot to fasten the device in place. The sleeve can be pulled tightly closed when this is done, thus causing the sleeve to surround the site of the connection in the flexible line tightly.

To fix the elongated portion in the slot, the elongated portion preferably has one or more barbs. If a plurality of barbs are provided, it is possible for the elongated portion to be fixed in different positions, thus enabling the portion in sleeve form of the device to be adapted to flexible lines or connecting systems of different dimensions. The barbs may also take the form of a continuous series of sawteeth.

In an alternative exemplary embodiment, the fastening means have an area which is provided with an adhesive or adhering layer. The adhesive or adhering layer is preferably a strip which is provided on the portion able to be deformed into a sleeve. The adhesive or adhering layer may for example also take the form of a hook-and-loop fastener.

Basically, the fastening means may be any means by which the relevant portions can, on the one hand, be connected together easily and can, on the other hand, be easily detached from one another. The fastening together of the relevant portions may for example be accomplished as a result of the forming of loops or straps, hooks or eyes, buttons and buttonholes or the like. A sliding-clasp fastener for example may even be provided for connecting the portions together.

In a further exemplary embodiment which is a particular preference, the elongated portion which is pulled through the slot is in particular a composite material comprising a textile material and a film. The stiffness of the strip can be increased by this composite material.

Increased security against the device according to the present invention slipping off is achieved if the arrangement for fixing the portion in sleeve form in place has a plurality of elongated portions. It is for example possible for two strips to be provided which enclose the connecting parts or the flexible line on both sides of the connecting system.

The device according to the present invention has connecting contacts to allow electrical contact to be made with the moisture sensor. The number of connecting contacts will depend on the form the moisture sensor takes. The moisture sensor may for example comprise two connecting contacts, the resistance between which is measured. Two further connecting contacts may also be provided to allow a terminal resistor to be connected. However, rather than a connecting strip having connecting contacts, it is also possible for an electrical connecting line which is then connected to the monitoring arrangement to be run from the device according to the present invention.

A preferred exemplary embodiment makes provision for the connecting contacts to be formed at the end of an elongated portion which is connected to the portion in the form of a sleeve. What is achieved in this way is that the connecting contacts are physically separated from the moisture sensor. There is therefore no need for the region in which the electrical contact is made to be sterile, unlike the region in which the moisture sensor is situated. This is particularly advantageous when central venous catheters are being monitored.

In a particularly preferred exemplary embodiment, the connecting contacts are arranged at the end of the elongated portion, which latter acts as a strip for pulling the portion in sleeve form closed. This makes it possible to dispense with an additional strip for making electrical contact with the moisture sensor.

The device according to the present invention preferably has a layer not permeable to moisture which is adjacent the patient and situated on the outside and a layer absorbent of liquid which is remote from the patient and situated on the inside. The electrically conductive structure of the moisture sensor is preferably embedded in the layer absorbent of liquid or is applied to the absorbent layer. The electrical conductive structure need not extend over the entire area of the absorbent layer because, due to the absorptive capacity of the layer, it is enough for moisture to be detected in a sub-region of the area.

In a particularly preferred exemplary embodiment, the absorbent layer in which the electrically conductive structure is to be embedded is a textile material. The textile material is preferably a woven material having non-conductive warp filaments and non-conductive weft filaments and conductive warp filaments and conductive weft filaments, which are so arranged that the electrically conductive structure is formed in the woven material. A woven material of this kind having an electrically conductive structure is described in detail in International Patent Publication No. WO 2011/116943.

The electrically conductive structure may have one or more conductors which, in a plurality of portions, extend at least over a sub-region of the portion in sleeve form.

The portion able to be deformed into a sleeve may be of different dimensions and shapes. In a preferred exemplary embodiment, the portion able to be deformed into a sleeve is a square-cornered portion which assumes the shape of a cylindrical portion which surrounds the flexible line or the connecting system.

An alternative exemplary embodiment makes provision for the portion deformable as a sleeve to be a circular portion which is cut away for part of its circumference. In this exemplary embodiment, the portion surrounding the flexible line assumes the shape of a funnel. For the flexible line to be passed through, the portion which is cut away for part of its circumference has in the centre a central, preferably circular, cut-out.

The device according to the present invention can be produced in large numbers by a weaving process without production involving any great cost or complication. It can also be cut away and sterilised with no great technical cost or complication and can be made available in sterile form in suitable packaging as a disposable sensor The arrangement according to the present invention for monitoring an access to a patient, and in particular for monitoring a vascular access in extra-corporeal blood treatment and particularly for monitoring a central venous catheter, has the device according to the present invention for detecting moisture, which is connected to the monitoring arrangement. The monitoring arrangement may trigger an audio and/or visual and/or tactile alarm if moisture is detected. It is also possible for a control signal to be generated for action in the control system controlling the system by which, via a flexible line, a liquid is fed to the patient and/or a liquid is fed out from the patient.

The arrangement according to the present invention for monitoring a patient access may form a separate unit or may be part of the system by which a liquid is fed to the patient and/or a liquid is fed out from the patient, and may in particular be part of the extra-corporeal blood treatment apparatus. If the monitoring arrangement according to the present invention is part of the blood treatment apparatus, the monitoring arrangement may make use of certain sub-assemblies or components which are present anyway in the blood treatment apparatus.

Exemplary embodiments of the device according to the present invention are explained in detail below with reference to the accompanying drawings.

BRIEF DESCRIPTION OF THE DRAWINGS

FIG. 9 is a simplified view of an eighth exemplary embodiment of device.

FIG. 10 is a simplified view of a ninth exemplary embodiment of device.

DETAILED DESCRIPTION

Figure 1:
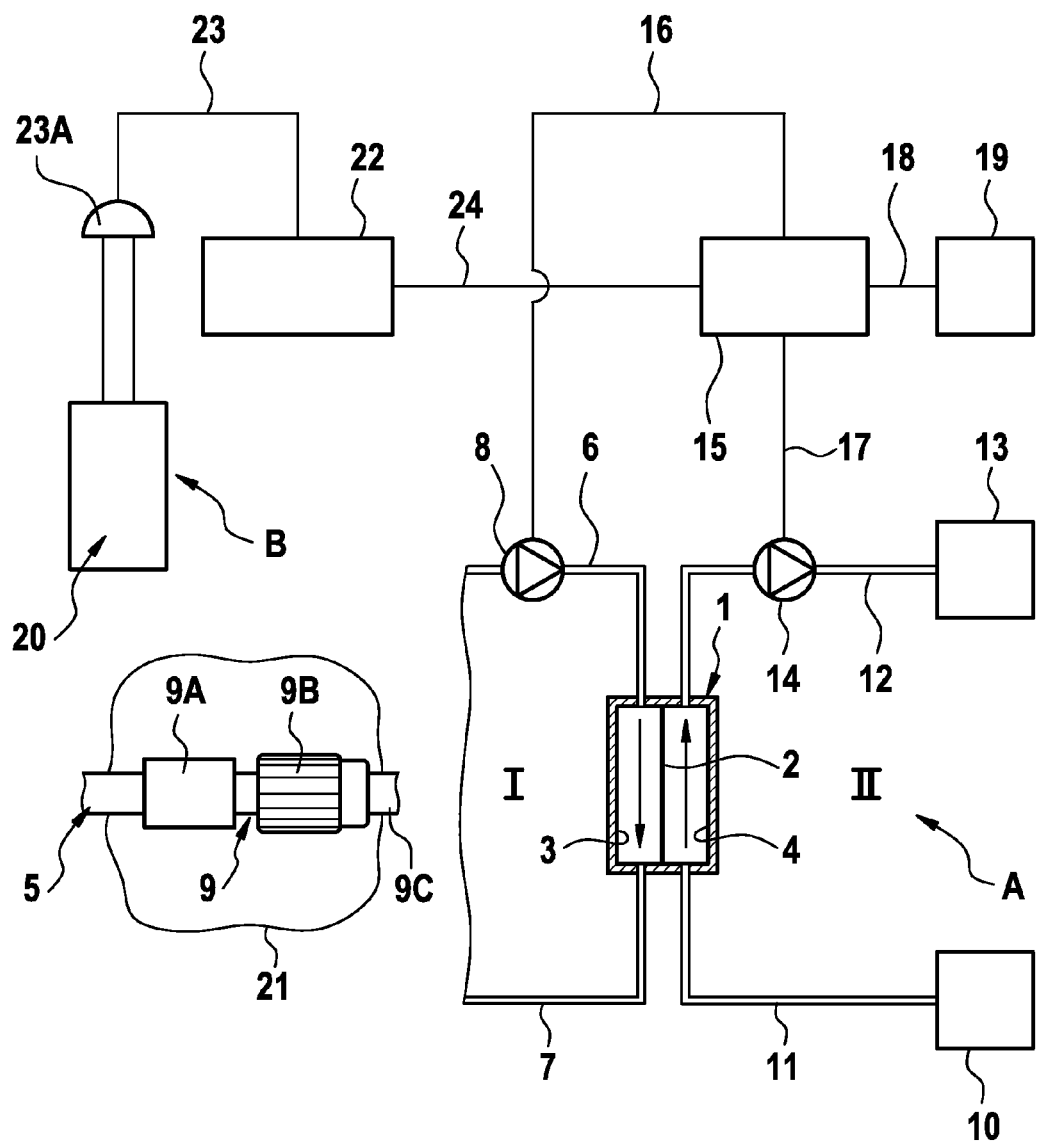
FIG. 1 shows the principal components of a blood treatment apparatus which has an arrangement for monitoring a vascular access.

FIG. 1 shows the principal components of a blood treatment apparatus, and in particular a haemodialysis apparatus A for acute dialysis, which has an arrangement B for monitoring a vascular access and in particular a vascular access which has a central venous catheter. The monitoring arrangement B is part of the haemodialysis apparatus A in the present embodiment. The dialysis apparatus will first be described by reference to FIG. 1.

The haemodialysis apparatus A has a dialyser 1 which is divided into a blood chamber 3 and a dialysis-fluid chamber 4 by a semi-permeable membrane 2. The vascular access to the patient is obtained by a central venous catheter 5 which is connected to the patient's neck. The central venous catheter 5 is part of the extra-corporeal blood circuit I, which is merely indicated and which includes the blood chamber 3 of the dialyser 1 and comprises the flexible lines 6, 7. A blood pump 8 is provided to pump the blood in the extra-corporeal circuit.

The dialysis-fluid circuit II of the dialysis apparatus A comprises a dialysis-fluid source 10 to which a dialysis-fluid infeed line 11, which runs to the inlet of the dialysis-fluid chamber 4 of the dialyser 1, is connected. Running off from the outlet of the dialysis-fluid chamber 4 of the dialyser 1 is a dialysis-fluid outfeed line 12 which runs to an outlet 13. A dialysis-fluid pump 14 is connected into the dialysis-fluid outfeed line 12.

Responsible for controlling the dialysis apparatus is a central control unit 15 which operates the blood and dialysis-fluid pumps 8, 14 via control lines 16, 17. The central control unit 15 is connected by a data line 18 to an alarm unit 19 which gives a visual and/or audio and/or tactile alarm if anything untoward happens.

In the present exemplary embodiment, the monitoring arrangement B, which is only shown schematically, is used to monitor a Luer lock connector 9 having parts 9A and 9B, for connecting the central venous catheter 5 to a flexible line 9C belonging to the extra-corporeal blood circuit I. The monitoring arrangement B has a device 20 for detecting moisture which is arranged at the point 21 of the connection to the flexible line. This device 20 is only shown in schematic form in FIG. 1. As well as this, the monitoring arrangement B also has an analysing arrangement 22 which is electrically connected to the device 20 by a connecting line 23. The connecting line 23 is connected to the device 20 by an electrical connector 23A.

The analysing arrangement 22 is connected to the central control unit 15 of the dialysis apparatus A by a data line 24. In the event of blood escaping from the point of connection 21 to the flexible line and wetting the device 20 for detecting moisture, the analysing arrangement 22 of the monitoring arrangement B generates a control signal which the central control unit 15 receives via the data line 24, the central control unit 15 then making an intervention in the blood treatment. The control unit 15 stops the blood pump 8 and generates an alarm signal so that the alarm unit 19 gives an audio and/or visual and/or tactile alarm.

Figure 2:
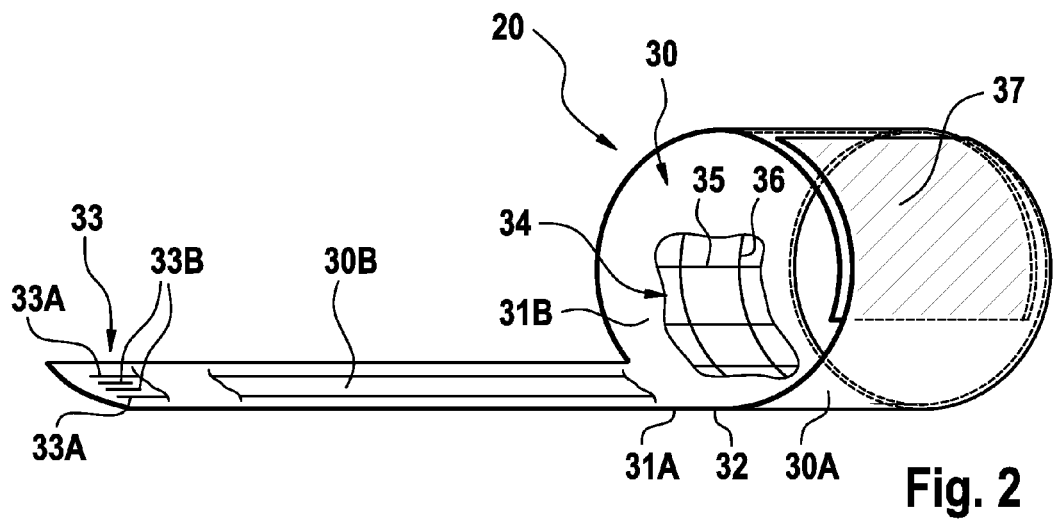
FIG. 2 is a simplified view of a first exemplary embodiment of device according to the present invention for detecting moisture which is fitted to a connecting system for connecting a central venous catheter to a flexible line.

FIG. 2 shows a first exemplary embodiment of device according to the present invention for detecting moisture. The device has a textile substrate material 30 which is a woven material in the exemplary embodiment. The woven material has a portion 30A in the form of a square-cornered blank which can be placed round the circumference of a flexible line or of a connecting system for connecting a catheter to a flexible line. Connected to one of the two long sides of the square-cornered portion 30A, in a central position between the two short sides, is an elongated portion 30B which acts as a connecting strip for a connector (not shown) for connecting the device according to the present invention to the analysing arrangement 22 of the arrangement B for monitoring the vascular access.

The absorbent woven material 30 has an outer side 31A adjacent the patient's skin and an inner side 31B remote from the patient's skin. On the outer side 31A, the woven material is connected, preferably over its entire area, to a film 32 of plastics material which is not permeable to liquid and is not electrically conductive. As well as this, the film 32 of plastics material also gives the woven material 30 the requisite strength and/or stiffness, particularly in the region of the elongated portion 30B for connection to the connector. As an alternative to the use of a film of plastics material, a hydrophobic coating may be provided on one side of the woven material. A polyester woven material can be made hydrophobic by for example the use of fluorine-containing gases in a low-pressure plasma.

The device for detecting moisture has a moisture sensor 34 which is merely indicated in FIG. 2 and which comprises an electrically conductive structure which is embedded in the woven material (FIG. 2). The woven material 30 comprises for this purpose non-conductive warp filaments and non-conductive weft filaments and conductive warp filaments and conductive weft filaments, which are so arranged as to produce the electrically conductive structure which is made up of a plurality of conductor portions 35, 36 positioned orthogonally to one another which are merely indicated. The individual portions of conductor 35, 36 extend over sub-regions of the square-cornered portion 30A able to be formed into a sleeve and run to the end of the elongated portion 30B for connection to the connector (not shown), the portions of conductor forming two electrodes. At the end of the elongated portion 30B, the portions of conductor take the form of connecting contacts 33. The outer connecting contacts 33A are used for the connection for measuring the resistance of the moisture sensor while the inner connecting contacts 33B are used as the connection for a terminal resistor.

Along one short side, the portion 30A able to be formed into a sleeve has an adhesive or adhering layer 37 in strip form which is indicated by a single-hatched area in FIG. 2. The adhesive or adhering layer 37 may also be provided along both short sides of the portion 30A, or it may be provided on the inside or outside of the portion 30A. What is crucial is for the portion 30A to be able to be placed around the circumference of the connecting system or the flexible line and for the portions which overlap one another to be able to be connected together when the portion 30A in sleeve form surrounds the connecting system or the flexible line tightly. The adhesive or adhering layer 37 may for example be a self-adhesive film or a hook-and-loop fastener. The film of plastics material which is applied to the outside of the woven material may for example take the form of an adhesive film in the edge region.

The device for detecting moisture can easily be removed again from the flexible line or the connecting system by releasing the adhesive or adhering layer connection, thus making the connecting system accessible again.

If the device for detecting moisture is placed against the flexible line or the connecting system, a leak will cause the woven material 30 to be wetted with moisture, such as blood for example, as a result of which the woven material will absorb a full charge of the liquid. This will change the resistance between the outer connecting contacts 33A of the electrically conductive structure. The sensor is sensitive wherever conductive filaments of the first electrode can be short-circuited by moisture to conductive filaments of the second electrode.

Figure 3:
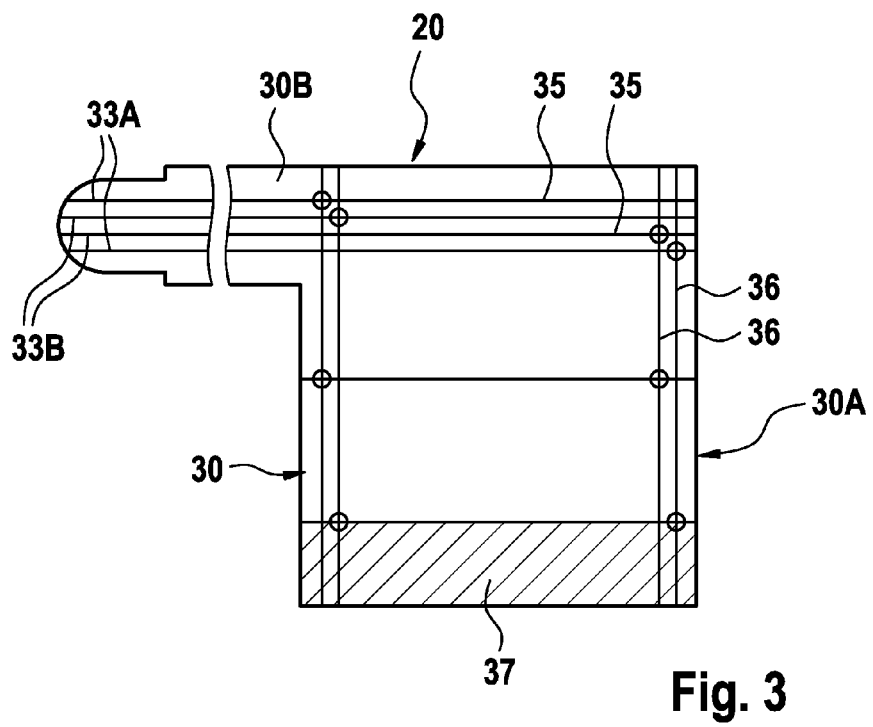
FIG. 3 shows a second exemplary embodiment of the device shown in FIG. 2 before being fitted to the connecting system.

FIG. 3 shows a second exemplary embodiment of the device 20 according to the present invention before it is placed against the flexible line or the latter's connecting system, i.e., when the device is not yet in the form of a sleeve. This exemplary embodiment differs from the first exemplary embodiment only in that the elongated portion 30B is connected to the square-cornered portion 30A not centrally but laterally. Parts which correspond to one another have therefore been identified by the same reference numerals. FIG. 3 clearly shows the portions of conductor 35, 36 which are positioned orthogonally to one another. The conductor portions 35, 36, which extend over sub-regions of the square-cornered portion 30A able to be formed into a sleeve, run to the end of the elongated portion 30B for connection to the connector (not shown). The intersections at which electrical contact is made in the woven material between the warp and weft filaments extending orthogonally to one another are identified by circles. A woven material of this kind having an electrically conductive structure is described in International Patent Publication No. WO 2011/116943, which is hereby incorporated by reference in its entirety.

FIGS. 4 to 10 show alternative exemplary embodiments of the device for detecting moisture which differ from the exemplary embodiments which have been described with reference to FIGS. 2 and 3 essentially in the form taken by the fastening means.

In the case of the exemplary embodiments shown in FIGS. 4 to 8, all that are shown are the outlines. The electrically conductive structure which is situated on the inside of the woven material has not been shown because the exemplary embodiments shown in FIGS. 4 to 8 differ from the exemplary embodiments shown in FIGS. 2 and 3 essentially only in the fastening means and the differing shape.

Figure 4:
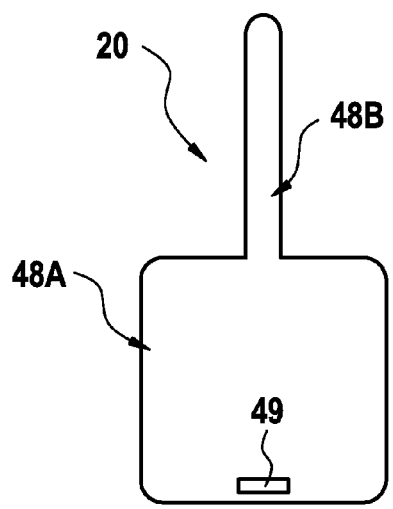
FIG. 4 is a simplified view of a third exemplary embodiment of device according to the present invention.

In the exemplary embodiment shown in FIG. 4, the portion 48A able to be formed into a sleeve is a substantially square-cornered portion. Connected to one of the sides of the square-cornered portion 48A in a central position is an elongated portion 48B which once again forms a connecting strip for a connector (not shown) for connecting the device for detecting moisture to the analysing arrangement of the monitoring arrangement. On the opposite side from the elongated portion 48B, the square-cornered portion 48A has a slot 49 whose width is slightly greater than the width of the elongated portion 48B. If the portion 48A is placed round the flexible line or the connecting system, the sleeve can be pulled tight by pulling the elongated portion 48B through the slot 49 and then fixing it in place. Hence, in this exemplary embodiment too, the elongated portion serves not only to fix the sleeve in place but also to connect up the moisture sensor electrically.

Figure 5:
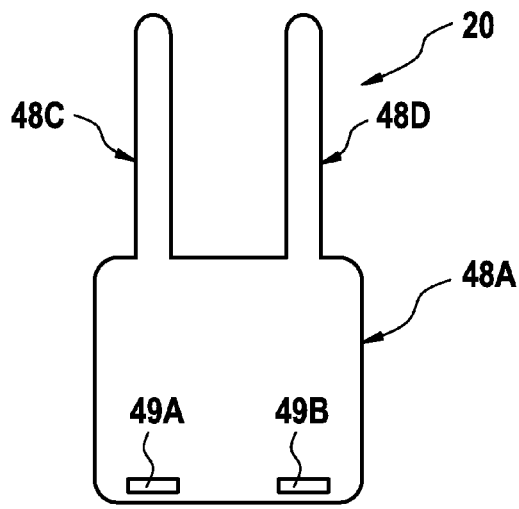
FIG. 5 is a simplified view of a fourth exemplary embodiment of device.

FIG. 5 shows an alternative exemplary embodiment which differs from the exemplary embodiment shown in FIG. 4 only in that instead of one central elongated portion being provided on one side of the square-cornered portion 48A there are two elongated portions 48C and 48D provided which are in off-center positions. Parts which correspond to one another have once again been given the same reference numerals. In the exemplary embodiment shown in FIG. 5, only one of the two elongated portions, such as the left-hand portion 48C for example, takes the form of a connecting strip for the connector. On the opposite side from the elongated portions 48C and 48D, the square-cornered portion 48A has two slots 49A and 49B arranged in off-center positions, through which the elongated portions 48C, 48D are pulled to pull the sleeve tight.

Figure 6:
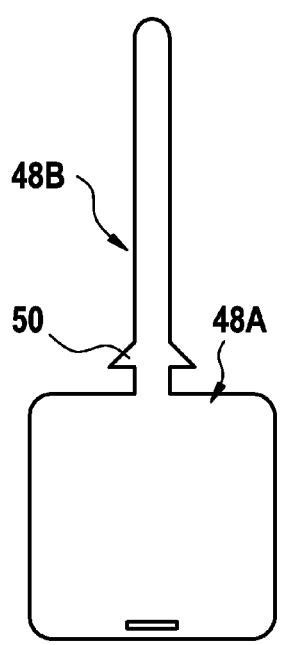
FIG. 6 is a simplified view of a fifth exemplary embodiment of device.
Figure 7:
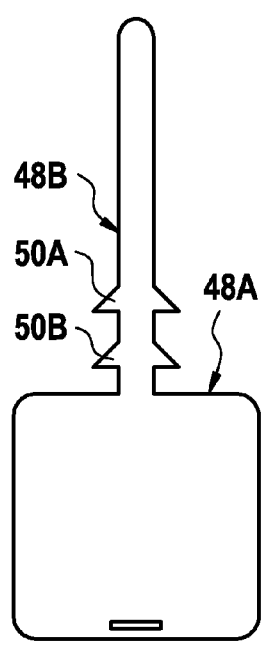
FIG. 7 is a simplified view of a sixth exemplary embodiment of device.
Figure 8:
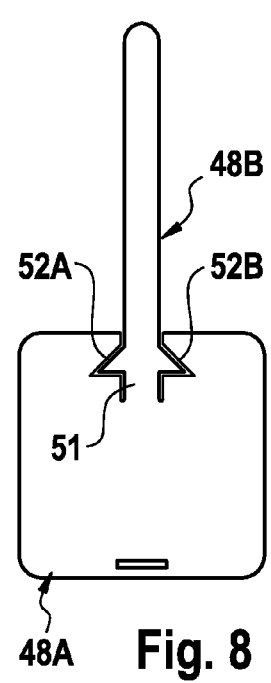
FIG. 8 is a simplified view of a seventh exemplary embodiment of device.

FIGS. 6 to 8 show alternative exemplary embodiments which differ from the exemplary embodiment shown in FIG. 4 only in the particular form taken by the elongated portion 48B. Whereas in the exemplary embodiment shown in FIG. 4 the elongated portion has to be fixed in place with additional fixing means, the elongated portion 48B in FIG. 6 has a barb 50 which prevents the elongated portion 48B from being pulled out of the slot 49 again. FIG. 7 shows an exemplary embodiment having two barbs 50A and 50B arranged at a distance from one another. It is however also possible for further barbs to be provided to enable the sleeve to be drawn together to the desired diameter.

FIG. 8 shows a further exemplary embodiment which differs from the exemplary embodiments described above only in that the barb 51 is incorporated in the square-cornered portion 48A. In the region in which the elongated portion 48B is connected to the square-cornered portion 48A, the said elongated portion 48B which is connected to the square-cornered portion 48A forms a cut-out in the square-cornered portion, the outline of the longitudinal sides of the elongated portion 48B being formed by incisions 52A, 52B in the square-cornered portion 48A. This allows the elongated portion 48B to be folded out of the square-cornered portion 48A to free the barb 51. It is also possible for a plurality of barbs to be formed in this way.

FIG. 9 shows an exemplary embodiment in which the portion 53 able to be formed into a sleeve is a circular portion which is cut away for part of its circumference. In the present exemplary embodiment, the circular portion 53 is cut away over an angle of 90°. In the center, the center portion 53 having the cut-away has a central circular cut-out 54 whose diameter is greater than the diameter of the flexible line or connecting system. Connected to one half of the circular portion 53 having the cut-away is an elongated portion 55 which once again forms the connecting strip for the electrical connector. Situated in the other half of the portion 53 are two slots 56A and 56B spaced apart from one another through which the elongated portion 55 can be pulled. In this exemplary embodiment, the elongated portion 55 can be fixed in place by being pulled through both the slots from above and below respectively. To fit the device 20 for detecting moisture, the circular portion 53 having the cut-away is placed around the flexible line or the connecting system, the flexible line or connecting system coming to rest in the central cut-out 54. The circular portion 53 having the cut-away is then shaped into a sleeve in the form of a funnel which surrounds the flexible line and the connecting system. The fixing in place is then performed with the connecting strip 55. The portions of conductor 35, 36 of the electrically conductive structure which forms the moisture sensor are shown in FIG. 9.

FIG. 10 shows an alternative exemplary embodiment which differs from the exemplary embodiment shown in FIG. 9 only in the arrangement of the conductor portions 35, 36 of the electrically conductive structure. In the exemplary embodiment shown in FIG. 10, the electrically conductive structure has not only the conductor portions 35, 36 but also additional conductor portions 35A, 36A, thus giving the moisture sensor shown in FIG. 10 greater sensitivity than the sensor shown in FIG. 9.

What is claimed is:

1. A device for detecting moisture for an arrangement for monitoring an access to a patient for a system by which, via a flexible line, a liquid is fed either to the patient or from the patient or both, or for monitoring a vascular access in extra-corporeal blood treatment, the device comprising:

a moisture sensor including an electrically conductive structure;

a portion deformable into a sleeve having a cylindrical shape and configured to be placed around a circumference of the flexible line or a connecting system for the flexible line, wherein the portion deformable into the sleeve includes on a first half of the portion deformable into the sleeve at least one slot extending from an inside of the portion to an outside of the portion deformable into the sleeve; and a fastening device for fixing the deformable sleeve portion in a position surrounding the flexible line or the connecting system, wherein the fastening device includes at least one elongated portion which extends in a central position or in an off-center position from a side of a second half of the portion deformable into the sleeve and is a composite material comprising a woven textile material and a nonpermeable film, wherein the at least one elongated portion is configured to be pulled through the at least one slot, wherein, to fix in place the at least one elongated portion which is pulled through the at least one slot, the at least one elongated portion includes one or more barbs which prevents the elongated portion from being pulled out of the slot, and wherein the electrically conductive structure is embedded in the woven textile material.

2. The device according to claim 1, wherein the fastening device includes an area or a strip provided with an adhesive or adhering layer.

3. The device according to claim 1, further comprising:
connecting contacts configured to allow electrical contact to be made with the moisture sensor, the connecting contacts being formed at an end of the elongated portion connected to the portion deformable into the sleeve.

4. The device according to claim 1, further comprising:
a layer not permeable to moisture which is adjacent the patient and situated on the outside of the portion deformable into the sleeve; and
a layer absorbent of liquid which is situated on the inside of the portion deformable into the sleeve.

5. The device according to claim 4, wherein the layer absorbent of liquid is a textile material including the electrically conductive structure.

6. The device according to claim 1, wherein the textile material is a woven material including non-conductive warp filaments, non-conductive weft filaments, conductive warp filaments and conductive weft filaments arranged such that the electrically conductive structure is formed in the woven material.

7. The device according to claim 1, wherein the electrically conductive structure has at least one conductor which, in a plurality of portions, extends at least over a sub-region of the portion in sleeve form.

8. The device according to claim 1, wherein the portion deformable into the sleeve is a square-cornered portion.

9. The device according to claim 1, wherein the portion deformable into the sleeve is a circular portion which is cut away for part of its circumference.

10. The device according to claim 9, wherein the circular portion includes a central cut-out in its center.

11. An arrangement for monitoring an access to a patient for a system by which, via a flexible line, a liquid is fed at least one of to the patient or from the patient, or for monitoring a vascular access in extra-corporeal blood treatment, the arrangement comprising:

the device for detecting moisture according to claim 1.

12. The device according to claim 1, wherein the electrically conductive structure has a plurality of conductors which, in a plurality of portions, extend at least over a sub-region of the portion in sleeve form, wherein at least one of the plurality of conductors also runs to the end of the elongate portion for connection to a connector.

13. The device according to claim 1, wherein the at least one elongated portion includes more than one barb which enables the sleeve to be drawn together to a desired diameter.

* * * * *